(12) United States Patent
Hannula et al.

(10) Patent No.: US 7,877,126 B2
(45) Date of Patent: *Jan. 25, 2011

(54) HAT-BASED OXIMETER SENSOR

(75) Inventors: Don Hannula, San Luis Obispo, CA (US); Paul Mannheimer, Danville, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1062 days.

This patent is subject to a terminal disclaimer.

(21) Appl. No.: 11/494,365

(22) Filed: Jul. 26, 2006

(65) Prior Publication Data

US 2006/0264723 A1 Nov. 23, 2006

Related U.S. Application Data

(60) Continuation of application No. 11/358,868, filed on Feb. 21, 2006, which is a division of application No. 10/606,668, filed on Jun. 25, 2003, now Pat. No. 7,047,056.

(51) Int. Cl.
*A61B 5/1455* (2006.01)
(52) U.S. Cl. ..................................... 600/344; 600/340
(58) Field of Classification Search ................. 600/310, 600/322, 323, 340, 344
See application file for complete search history.

(56) References Cited

U.S. PATENT DOCUMENTS

| | | | |
|---|---|---|---|
| 4,025,733 A | 5/1977 | Klar et al. | |
| 4,047,400 A | 9/1977 | Thorneburg | |
| 4,321,930 A | * 3/1982 | Jobsis et al. | ................. 600/344 |
| 4,462,116 A | 7/1984 | Sanzone et al. | |
| 4,499,741 A | 2/1985 | Harris | |
| 4,510,938 A | 4/1985 | Jobsis et al. | |
| 4,570,638 A | 2/1986 | Stoddart et al. | |
| 4,675,919 A | 6/1987 | Heine et al. | |
| 4,739,757 A | 4/1988 | Edwards | |
| 4,775,116 A | 10/1988 | Klein | |
| 4,784,162 A | 11/1988 | Ricks et al. | |

(Continued)

FOREIGN PATENT DOCUMENTS

CN 1306260 8/2001

(Continued)

OTHER PUBLICATIONS

U.S. Appl. No. 10/677,742, filed Oct. 1, 2003, Hannula et al.

(Continued)

*Primary Examiner*—Eric F Winakur
(74) *Attorney, Agent, or Firm*—Fletcher Yoder

(57) ABSTRACT

A method for use and an improved oximeter sensor substrate that is conforming to the shape of the patient's forehead. In one embodiment, the present invention is an oximeter sensor, having a substrate with a shape similar to a shape of at least a portion of a patient's forehead and including a section adapted to substantially fit over a portion of a forehead of a patient; an emitter disposed on the substrate at a position located on the section; and a detector disposed on the substrate at a distance from the emitter. In one embodiment, the substrate includes a hat that holds the emitter and the detector in a spaced-part manner against the patient's forehead.

19 Claims, 3 Drawing Sheets

U.S. PATENT DOCUMENTS

| | | | |
|---|---|---|---|
| 4,802,485 A | 2/1989 | Bowers et al. | |
| 4,825,872 A | 5/1989 | Tan et al. | |
| 4,825,879 A | 5/1989 | Tan et al. | |
| 4,833,734 A | 5/1989 | Der Estephanian | |
| 4,838,279 A | 6/1989 | Fore | |
| 4,856,116 A | 8/1989 | Sullivan | |
| 4,890,619 A | 1/1990 | Hatschek | |
| 4,910,804 A | 3/1990 | Lidgren | |
| 4,918,758 A | 4/1990 | Rendina | |
| 4,930,888 A | 6/1990 | Feisleben et al. | |
| 4,942,877 A | 7/1990 | Sakai et al. | |
| 4,972,331 A | 11/1990 | Chance | |
| 4,977,011 A | 12/1990 | Smith | |
| 4,991,234 A | 2/1991 | Greenberg | |
| 4,996,975 A | 3/1991 | Nakamura | |
| 5,005,374 A | 4/1991 | Spitler et al. | |
| 5,040,540 A * | 8/1991 | Sackner | 600/485 |
| 5,054,488 A | 10/1991 | Muz | |
| 5,080,096 A | 1/1992 | Hooper et al. | |
| 5,080,098 A | 1/1992 | Willett et al. | |
| H1039 H | 4/1992 | Tripp, Jr. et al. | |
| 5,111,817 A | 5/1992 | Clark et al. | |
| 5,119,815 A | 6/1992 | Chance | |
| 5,122,974 A | 6/1992 | Chance | |
| 5,125,403 A | 6/1992 | Culp | |
| 5,167,230 A | 12/1992 | Chance | |
| 5,188,108 A | 2/1993 | Secker | |
| 5,191,891 A | 3/1993 | Righter | |
| 5,209,230 A | 5/1993 | Swedlow et al. | |
| 5,214,409 A | 5/1993 | Beigel | |
| 5,217,012 A | 6/1993 | Young et al. | |
| 5,217,013 A | 6/1993 | Lewis et al. | |
| 5,241,300 A | 8/1993 | Buschmann | |
| 5,246,003 A | 9/1993 | DeLonzor | |
| 5,253,645 A | 10/1993 | Friedman et al. | |
| 5,267,563 A | 12/1993 | Swedlow et al. | |
| 5,267,567 A | 12/1993 | Aung et al. | |
| 5,295,490 A | 3/1994 | Dodakian | |
| 5,313,940 A | 5/1994 | Fuse et al. | |
| 5,337,744 A | 8/1994 | Branigan | |
| 5,348,008 A | 9/1994 | Bornn et al. | |
| 5,353,798 A | 10/1994 | Sieben | |
| 5,354,979 A | 10/1994 | Adelson et al. | |
| 5,357,953 A | 10/1994 | Merrick et al. | |
| 5,368,025 A | 11/1994 | Young et al. | |
| 5,368,562 A | 11/1994 | Blomquist et al. | |
| 5,383,874 A | 1/1995 | Jackson et al. | |
| 5,392,777 A | 2/1995 | Swedlow et al. | |
| 5,398,689 A | 3/1995 | Connor et al. | |
| 5,400,267 A | 3/1995 | Denen et al. | |
| 5,405,269 A | 4/1995 | Stupecky | |
| 5,405,614 A | 4/1995 | D'Angelo et al. | |
| 5,413,099 A | 5/1995 | Schmidt et al. | |
| 5,413,101 A | 5/1995 | Sugiura | |
| 5,413,102 A | 5/1995 | Schmidt et al. | |
| 5,415,166 A | 5/1995 | Imran | |
| 5,425,360 A | 6/1995 | Nelson | |
| 5,431,170 A | 7/1995 | Mathews | |
| 5,437,275 A | 8/1995 | Amundsen et al. | |
| 5,437,634 A | 8/1995 | Amano | |
| 5,444,254 A | 8/1995 | Thomson | |
| 5,451,763 A | 9/1995 | Pickett et al. | |
| 5,452,717 A | 9/1995 | Branigan et al. | |
| 5,465,714 A | 11/1995 | Scheuing | |
| 5,469,845 A | 11/1995 | DeLonzor et al. | |
| 5,482,034 A | 1/1996 | Lewis et al. | |
| 5,490,523 A | 2/1996 | Isaacson et al. | |
| 5,507,752 A * | 4/1996 | Elliott | 606/123 |
| 5,528,519 A | 6/1996 | Onkura et al. | |
| 5,546,955 A | 8/1996 | Wilk | |
| 5,551,423 A | 9/1996 | Sugiura | |
| 5,562,718 A | 10/1996 | Palermo | |
| 5,564,108 A | 10/1996 | Hunsaker et al. | |
| 5,564,417 A | 10/1996 | Chance | |
| 5,584,296 A | 12/1996 | Cui et al. | |
| 5,592,408 A | 1/1997 | Keskin et al. | |
| 5,596,987 A | 1/1997 | Chance | |
| 5,617,865 A | 4/1997 | Palczewska et al. | |
| 5,617,866 A | 4/1997 | Marian, Jr. | |
| 5,627,323 A | 5/1997 | Stern | |
| 5,634,466 A | 6/1997 | Gruner | |
| 5,638,593 A | 6/1997 | Gerhardt et al. | |
| 5,638,818 A | 6/1997 | Diab et al. | |
| 5,640,953 A | 6/1997 | Bishop et al. | |
| 5,645,440 A | 7/1997 | Tobler et al. | |
| 5,645,586 A | 7/1997 | Meltzer | |
| 5,646,416 A | 7/1997 | Vande Velde | |
| 5,671,750 A | 9/1997 | Shinoda | |
| 5,673,708 A | 10/1997 | Athanasiou et al. | |
| 5,678,544 A | 10/1997 | DeLonzor et al. | |
| 5,681,285 A | 10/1997 | Ford et al. | |
| 5,683,434 A | 11/1997 | Archer | |
| 5,697,363 A | 12/1997 | Hart | |
| 5,697,367 A | 12/1997 | Lewis et al. | |
| 5,701,894 A | 12/1997 | Cherry et al. | |
| 5,706,820 A | 1/1998 | Hossack et al. | |
| 5,732,475 A | 3/1998 | Sacks et al. | |
| 5,738,612 A | 4/1998 | Tsuda | |
| 5,743,856 A | 4/1998 | Oka et al. | |
| 5,743,857 A | 4/1998 | Shinoda et al. | |
| 5,752,913 A | 5/1998 | Oka | |
| 5,752,920 A | 5/1998 | Ogura et al. | |
| 5,758,644 A | 6/1998 | Diab et al. | |
| 5,772,601 A | 6/1998 | Oka et al. | |
| 5,776,058 A | 7/1998 | Levinson et al. | |
| 5,776,071 A | 7/1998 | Inuka et al. | |
| 5,779,631 A | 7/1998 | Chance | |
| 5,779,639 A | 7/1998 | Yeung | |
| 5,782,757 A | 7/1998 | Diab et al. | |
| 5,786,592 A | 7/1998 | Hök | |
| 5,791,347 A | 8/1998 | Flaherty et al. | |
| 5,791,348 A | 8/1998 | Aung et al. | |
| 5,792,052 A | 8/1998 | Isaacson et al. | |
| 5,792,058 A | 8/1998 | Lee et al. | |
| 5,797,841 A | 8/1998 | Delonzer et al. | |
| 5,810,724 A | 9/1998 | Gronvall | |
| 5,813,980 A | 9/1998 | Levinson et al. | |
| 5,817,008 A * | 10/1998 | Rafert et al. | 600/323 |
| 5,823,012 A | 10/1998 | Hacskaylo | |
| 5,823,952 A | 10/1998 | Levinson et al. | |
| 5,826,277 A | 10/1998 | McConville | |
| 5,830,136 A | 11/1998 | Delonzer et al. | |
| 5,830,137 A | 11/1998 | Scharf | |
| 5,830,148 A | 11/1998 | Inukai et al. | |
| 5,830,149 A | 11/1998 | Oka et al. | |
| 5,833,602 A | 11/1998 | Osemwota | |
| 5,836,887 A | 11/1998 | Oka et al. | |
| 5,839,439 A | 11/1998 | Nierlich et al. | |
| RE36,000 E | 12/1998 | Swedlow et al. | |
| 5,842,981 A | 12/1998 | Larsen et al. | |
| 5,842,982 A | 12/1998 | Mannheimer | |
| 5,851,179 A | 12/1998 | Ritson et al. | |
| 5,857,974 A | 1/1999 | Eberuie et al. | |
| 5,860,932 A | 1/1999 | Goto et al. | |
| 5,860,957 A | 1/1999 | Jacobsen et al. | |
| 5,868,133 A | 2/1999 | DeVries et al. | |
| 5,870,626 A | 2/1999 | Lebeau | |
| 5,872,713 A | 2/1999 | Douglas et al. | |
| 5,873,821 A | 2/1999 | Chance et al. | |
| 5,879,294 A | 3/1999 | Anderson et al. | |
| 5,891,021 A | 4/1999 | Dillon et al. | |
| 5,891,026 A | 4/1999 | Wang et al. | |
| 5,895,359 A | 4/1999 | Peel, II | |
| 5,902,235 A | 5/1999 | Lewis et al. | |

| | | | | | | |
|---|---|---|---|---|---|---|
| 5,906,581 A | 5/1999 | Tsuda | | 6,263,223 B1 | 7/2001 | Shepherd et al. |
| 5,913,819 A | 6/1999 | Taylor et al. | | 6,280,213 B1 | 8/2001 | Tobler et al. |
| 5,916,154 A | 6/1999 | Hobbs et al. | | 6,282,450 B1 | 8/2001 | Hartlaub et al. |
| 5,919,133 A | 7/1999 | Taylor et al. | | 6,283,922 B1 | 9/2001 | Goto et al. |
| 5,931,789 A * | 8/1999 | Alfano et al. .............. 600/310 | | 6,285,895 B1 | 9/2001 | Ristolainen et al. |
| 5,931,790 A | 8/1999 | Peel, II | | 6,306,076 B1 | 10/2001 | Gill |
| 5,931,791 A | 8/1999 | Saltzstein et al. | | 6,308,089 B1 | 10/2001 | von der Ruhr et al. |
| 5,934,925 A | 8/1999 | Tobler et al. | | 6,321,100 B1 | 11/2001 | Parker |
| 5,936,539 A | 8/1999 | Fuchs | | 6,322,516 B1 | 11/2001 | Masuda et al. |
| 5,947,905 A | 9/1999 | Hadjicostis et al. | | 6,343,223 B1 | 1/2002 | Chin |
| 5,954,053 A | 9/1999 | Chance et al. | | 6,343,224 B1 | 1/2002 | Parker |
| 5,957,850 A | 9/1999 | Marian, Jr. | | 6,346,886 B1 | 2/2002 | DeLa Huerga |
| 5,964,701 A | 10/1999 | Asada et al. | | 6,349,228 B1 | 2/2002 | Kiani et al. |
| 5,980,464 A | 11/1999 | Tsuda | | 6,356,774 B1 | 3/2002 | Bernstein et al. |
| 5,983,129 A | 11/1999 | Cowan et al. | | 6,362,622 B1 | 3/2002 | Stauber et al. |
| 5,987,343 A | 11/1999 | Kinast | | 6,368,282 B1 | 4/2002 | Oka et al. |
| 5,987,351 A | 11/1999 | Chance | | 6,370,411 B1 | 4/2002 | Osadchy et al. |
| 5,991,648 A | 11/1999 | Levin | | 6,377,829 B1 | 4/2002 | Al-Ali |
| 5,995,077 A | 11/1999 | Wilcox et al. | | 6,381,480 B1 | 4/2002 | Stoddart et al. |
| 5,995,855 A | 11/1999 | Kiani et al. | | 6,381,481 B1 | 4/2002 | Levendowski et al. |
| 5,995,856 A | 11/1999 | Mannheimer et al. | | 6,385,486 B1 | 5/2002 | John et al. |
| 5,995,857 A | 11/1999 | Toomim et al. | | 6,385,821 B1 | 5/2002 | Medgil et al. |
| 6,007,492 A | 12/1999 | Goto et al. | | 6,387,092 B1 | 5/2002 | Burnside et al. |
| 6,011,986 A | 1/2000 | Diab et al. | | 6,388,240 B2 | 5/2002 | Schulz et al. |
| 6,022,320 A | 2/2000 | Ogura et al. | | 6,397,091 B2 | 5/2002 | Diab et al. |
| 6,027,453 A | 2/2000 | Miwa et al. | | 6,405,075 B1 | 6/2002 | Levin |
| 6,030,351 A | 2/2000 | Schmidt et al. | | 6,416,471 B1 | 7/2002 | Kumar et al. |
| 6,031,603 A | 2/2000 | Fine et al. | | 6,416,474 B1 | 7/2002 | Penner et al. |
| 6,036,651 A | 3/2000 | Inukai et al. | | 6,417,774 B1 | 7/2002 | Hibbs et al. |
| 6,041,247 A | 3/2000 | Weckstrom et al. | | 6,423,010 B1 | 7/2002 | Friedman et al. |
| 6,047,201 A | 4/2000 | Jackson, III | | 6,430,423 B2 | 8/2002 | DeLonzer et al. |
| 6,047,203 A | 4/2000 | Sackner et al. | | 6,432,050 B1 | 8/2002 | Porat et al. |
| 6,049,958 A | 4/2000 | Eberle et al. | | 6,450,168 B1 | 9/2002 | Nguyen |
| 6,050,951 A | 4/2000 | Friedman et al. | | 6,450,957 B1 | 9/2002 | Yoshimi et al. |
| 6,052,619 A | 4/2000 | John | | 6,450,981 B1 | 9/2002 | Shabty et al. |
| 6,073,038 A | 6/2000 | Wang et al. | | 6,454,708 B1 | 9/2002 | Ferguson et al. |
| 6,084,380 A | 7/2000 | Burton | | 6,456,862 B2 * | 9/2002 | Benni .................. 600/331 |
| 6,085,752 A | 7/2000 | Kehr et al. | | 6,461,305 B1 | 10/2002 | Schnall |
| 6,088,607 A | 7/2000 | Diab et al. | | 6,463,310 B1 | 10/2002 | Swedlow et al. |
| 6,106,780 A | 8/2000 | Douglas et al. | | 6,466,809 B1 | 10/2002 | Riley |
| 6,112,107 A | 8/2000 | Hannula | | 6,468,241 B1 | 10/2002 | Gelfand et al. |
| 6,115,621 A | 9/2000 | Chin | | 6,470,199 B1 | 10/2002 | Kopotic et al. |
| 6,118,382 A | 9/2000 | Hibbs et al. | | 6,470,279 B1 | 10/2002 | Samsoondar |
| 6,134,459 A | 10/2000 | Roberts et al. | | 6,480,762 B1 | 11/2002 | Uchikubo et al. |
| 6,144,868 A | 11/2000 | Parker | | 6,491,638 B2 | 12/2002 | Oka |
| 6,149,481 A | 11/2000 | Wang et al. | | 6,491,639 B1 | 12/2002 | Turcott |
| 6,152,754 A | 11/2000 | Gerhardt et al. | | 6,503,087 B1 | 1/2003 | Eggert et al. |
| 6,154,667 A | 11/2000 | Miura et al. | | 6,503,204 B1 | 1/2003 | Sumanaweera et al. |
| 6,162,188 A | 12/2000 | Barnea | | 6,505,061 B2 | 1/2003 | Larson |
| 6,165,173 A | 12/2000 | Kamdar et al. | | 6,511,478 B1 | 1/2003 | Burnside et al. |
| 6,171,258 B1 | 1/2001 | Karakasoglu et al. | | 6,516,289 B2 | 2/2003 | David |
| 6,173,196 B1 | 1/2001 | Delonzer et al. | | 6,519,487 B1 | 2/2003 | Parker |
| 6,179,786 B1 | 1/2001 | Young | | 6,524,257 B2 | 2/2003 | Ogura |
| 6,181,959 B1 | 1/2001 | Schollermann et al. | | 6,525,386 B1 | 2/2003 | Mills et al. |
| 6,184,521 B1 | 2/2001 | Coffin, IV et al. | | 6,526,309 B1 | 2/2003 | Chance |
| 6,186,953 B1 | 2/2001 | Narimatsu | | 6,526,970 B2 | 3/2003 | DeVries et al. |
| 6,186,954 B1 | 2/2001 | Narimatsu | | 6,527,725 B1 | 3/2003 | Inukai et al. |
| 6,190,325 B1 | 2/2001 | Narimatsu | | 6,527,726 B1 | 3/2003 | Goto et al. |
| 6,196,974 B1 | 3/2001 | Miwa | | 6,535,765 B1 | 3/2003 | Amely-Velez et al. |
| 6,198,952 B1 | 3/2001 | Miesel | | 6,537,220 B1 | 3/2003 | Friemel et al. |
| 6,199,550 B1 | 3/2001 | Wiesmann et al. | | 6,541,756 B2 | 4/2003 | Schulz et al. |
| 6,209,144 B1 | 4/2001 | Carter | | 6,542,081 B2 | 4/2003 | Torch |
| 6,216,021 B1 | 4/2001 | Franceschini et al. | | 6,547,743 B2 | 4/2003 | Brydon |
| 6,223,063 B1 | 4/2001 | Chaiken et al. | | 6,551,252 B2 | 4/2003 | Sackner et al. |
| 6,241,680 B1 | 4/2001 | Miwa | | 6,553,242 B1 | 4/2003 | Sarussi |
| 6,248,083 B1 | 6/2001 | Smith et al. | | 6,575,902 B1 | 6/2003 | Burton |
| 6,251,076 B1 | 6/2001 | Hovland et al. | | 6,577,884 B1 * | 6/2003 | Boas .................. 600/310 |
| 6,251,080 B1 | 6/2001 | Henkin et al. | | 6,580,086 B1 | 6/2003 | Schulz et al. |
| 6,251,081 B1 | 6/2001 | Narimatsu | | 6,582,371 B2 | 6/2003 | Miller |
| 6,251,113 B1 | 6/2001 | Appelbaum et al. | | 6,582,374 B2 | 6/2003 | Yokozeki |
| 6,256,523 B1 | 7/2001 | Diab et al. | | 6,584,356 B2 | 6/2003 | Wassmund et al. |
| 6,256,524 B1 | 7/2001 | Walker et al. | | 6,589,171 B2 | 7/2003 | Keirsbilck |
| 6,263,221 B1 | 7/2001 | Chance et al. | | 6,589,183 B2 | 7/2003 | Yokozeki |

| Patent | Date | Inventors |
|---|---|---|
| 6,589,189 B2 | 7/2003 | Meyerson et al. |
| 6,594,513 B1 | 7/2003 | Jobsis et al. |
| 6,597,933 B2 | 7/2003 | Kiani et al. |
| 6,605,038 B1 | 8/2003 | Teller et al. |
| 6,606,993 B1 | 8/2003 | Wiesmann et al. |
| 6,611,793 B1 | 8/2003 | Burnside et al. |
| 6,615,065 B1 | 9/2003 | Barrett et al. |
| 6,622,034 B1 | 9/2003 | Gorski et al. |
| 6,626,537 B1 * | 9/2003 | Odom et al. ............... 600/318 |
| 6,635,048 B1 | 10/2003 | Ullestad et al. |
| 6,645,154 B2 | 11/2003 | Oka |
| 6,645,155 B2 | 11/2003 | Inukai et al. |
| 6,654,622 B1 | 11/2003 | Eberhard et al. |
| 6,666,860 B1 | 12/2003 | Takahashi |
| 6,671,531 B2 | 12/2003 | Al-Ali et al. |
| 6,678,543 B2 | 1/2004 | Diab et al. |
| 6,681,454 B2 | 1/2004 | Modgil et al. |
| 6,684,091 B2 | 1/2004 | Parker |
| 6,694,160 B2 | 2/2004 | Chin |
| 6,700,497 B2 | 3/2004 | Hibbs et al. |
| 6,704,601 B1 | 3/2004 | Amely-Velez et al. |
| 6,708,048 B1 | 3/2004 | Chance |
| 6,711,425 B1 | 3/2004 | Reuss |
| 6,712,767 B2 | 3/2004 | Hossack et al. |
| 6,721,585 B1 | 4/2004 | Parker |
| 6,721,602 B2 | 4/2004 | Engmark et al. |
| 6,725,075 B2 | 4/2004 | Al-Ali |
| 6,726,327 B2 | 4/2004 | Torrey et al. |
| 6,731,963 B2 | 5/2004 | Finarov et al. |
| 6,735,459 B2 | 5/2004 | Parker |
| 6,736,759 B1 | 5/2004 | Stubbs et al. |
| 6,736,786 B1 | 5/2004 | Shabty et al. |
| 6,743,173 B2 | 6/2004 | Penner et al. |
| 6,743,202 B2 | 6/2004 | Hirschman et al. |
| 6,745,061 B1 | 6/2004 | Hicks et al. |
| 6,748,254 B2 | 6/2004 | O'Neil et al. |
| 6,763,255 B2 | 7/2004 | DeLonzor et al. |
| 6,771,994 B2 | 8/2004 | Kiani et al. |
| 6,776,758 B2 | 8/2004 | Peszynski et al. |
| 6,779,257 B2 | 8/2004 | Kiepen et al. |
| 6,792,300 B1 | 9/2004 | Diab et al. |
| 6,796,946 B2 | 9/2004 | Ogura et al. |
| 6,804,543 B2 | 10/2004 | Miller et al. |
| 6,808,496 B2 | 10/2004 | Oka et al. |
| 6,811,538 B2 | 11/2004 | Westbrook et al. |
| 6,813,511 B2 | 11/2004 | Diab et al. |
| 6,824,520 B2 | 11/2004 | Orr et al. |
| 6,827,688 B2 | 12/2004 | Goto et al. |
| 6,830,711 B2 | 12/2004 | Mills et al. |
| 6,832,987 B2 | 12/2004 | David et al. |
| 6,842,722 B2 | 1/2005 | David |
| 6,847,294 B1 | 1/2005 | Lin et al. |
| 6,849,074 B2 | 2/2005 | Chen et al. |
| 6,853,304 B2 | 2/2005 | Reisman et al. |
| 6,870,479 B2 | 3/2005 | Gabriel |
| 6,893,400 B2 | 5/2005 | Kawaguchi et al. |
| 6,898,299 B1 | 5/2005 | Brooks |
| 6,904,124 B2 | 6/2005 | Staver et al. |
| 6,909,912 B2 | 6/2005 | Melker |
| 6,911,027 B1 | 6/2005 | Edwards et al. |
| 6,920,345 B2 | 7/2005 | Al-Ali et al. |
| 6,921,198 B2 | 7/2005 | Gruszecki et al. |
| 6,923,771 B2 | 8/2005 | Ogura et al. |
| 6,923,776 B2 | 8/2005 | Shabty et al. |
| 6,930,608 B2 | 8/2005 | Grajales et al. |
| 6,934,570 B2 | 8/2005 | Kiani et al. |
| 6,934,571 B2 | 8/2005 | Wiesmann et al. |
| 6,936,011 B2 | 8/2005 | Sheldon |
| 6,939,314 B2 | 9/2005 | Hall et al. |
| 6,943,881 B2 | 9/2005 | Wang |
| 6,955,650 B2 | 10/2005 | Mault et al. |
| 6,965,071 B2 | 11/2005 | Watchko et al. |
| 6,971,790 B2 | 12/2005 | Quinn et al. |
| 6,985,763 B2 | 1/2006 | Boas et al. |
| 6,985,764 B2 | 1/2006 | Mason et al. |
| 6,990,371 B2 | 1/2006 | Powers et al. |
| 6,993,371 B2 | 1/2006 | Kiani et al. |
| 6,995,665 B2 | 2/2006 | Appelt et al. |
| 7,001,334 B2 | 2/2006 | Reed et al. |
| 7,018,338 B2 | 3/2006 | Vetter et al. |
| 7,020,508 B2 | 3/2006 | Stivoric et al. |
| 7,024,235 B2 | 4/2006 | Melker et al. |
| 7,027,850 B2 | 4/2006 | Wasserman |
| 7,027,871 B2 | 4/2006 | Burnes et al. |
| 7,039,449 B2 | 5/2006 | Al-Ali |
| 7,041,121 B1 | 5/2006 | Williams et al. |
| 7,047,054 B2 | 5/2006 | Benni |
| 7,047,055 B2 | 5/2006 | Boas et al. |
| 7,047,056 B2 | 5/2006 | Hannula et al. |
| 7,048,687 B1 | 5/2006 | Reuss et al. |
| 7,054,453 B2 | 5/2006 | Causevic et al. |
| 7,054,454 B2 | 5/2006 | Causevic et al. |
| 7,063,669 B2 | 6/2006 | Brawner et al. |
| 7,067,893 B2 | 6/2006 | Mills et al. |
| 7,072,704 B2 | 7/2006 | Bucholz et al. |
| 7,079,036 B2 | 7/2006 | Cooper et al. |
| 7,085,597 B2 | 8/2006 | Fein et al. |
| 7,087,023 B2 | 8/2006 | Daft et al. |
| 7,089,061 B2 | 8/2006 | Grey |
| 7,096,052 B2 | 8/2006 | Mason et al. |
| 7,096,054 B2 | 8/2006 | Abdul-Hafiz et al. |
| 7,097,621 B2 | 8/2006 | Narimatsu et al. |
| 7,107,706 B1 | 9/2006 | Bailey et al. |
| 7,113,815 B2 | 9/2006 | O'Neil et al. |
| RE39,359 E | 10/2006 | McGraw et al. |
| 7,127,278 B2 | 10/2006 | Melker et al. |
| 7,132,641 B2 | 11/2006 | Schulz et al. |
| 7,136,452 B2 | 11/2006 | Spartiotis et al. |
| 7,171,251 B2 | 1/2007 | Sarussi et al. |
| 7,181,264 B2 | 2/2007 | Wiesmann et al. |
| 7,204,250 B1 | 4/2007 | Burton |
| 7,220,220 B2 | 5/2007 | Stubbs et al. |
| 7,245,953 B1 | 7/2007 | Parker |
| 7,248,910 B2 | 7/2007 | Li |
| 7,289,837 B2 | 10/2007 | Mannheimer et al. |
| 7,297,119 B2 | 11/2007 | Westbrook et al. |
| 7,313,427 B2 | 12/2007 | Benni |
| 7,349,726 B2 | 3/2008 | Casciani et al. |
| 7,376,454 B2 | 5/2008 | Casciani et al. |
| 7,415,298 B2 | 8/2008 | Casciani et al. |
| 2001/0000790 A1 | 5/2001 | Delonzer et al. |
| 2001/0009265 A1 | 7/2001 | Schulz et al. |
| 2001/0009398 A1 | 7/2001 | Sekura et al. |
| 2001/0028309 A1 | 10/2001 | Torch |
| 2001/0029325 A1 | 10/2001 | Parker |
| 2001/0034506 A1 | 10/2001 | Hirschman et al. |
| 2001/0037068 A1 | 11/2001 | Goto et al. |
| 2001/0045532 A1 | 11/2001 | Schulz et al. |
| 2001/0047126 A1 | 11/2001 | Nagai et al. |
| 2001/0048466 A1 | 12/2001 | Takami |
| 2001/0051773 A1 | 12/2001 | Oka |
| 2002/0005197 A1 | 1/2002 | DeVries et al. |
| 2002/0013538 A1 | 1/2002 | Teller |
| 2002/0013613 A1 | 1/2002 | Haller et al. |
| 2002/0026107 A1 | 2/2002 | Kiani et al. |
| 2002/0026109 A1 | 2/2002 | Diab et al. |
| 2002/0032386 A1 | 3/2002 | Sackner et al. |
| 2002/0038082 A1 | 3/2002 | Chin |
| 2002/0042558 A1 | 4/2002 | Mendelson |
| 2002/0045807 A1 | 4/2002 | Al-Ali et al. |
| 2002/0049372 A1 | 4/2002 | Diab |
| 2002/0052539 A1 | 5/2002 | Haller et al. |
| 2002/0052552 A1 | 5/2002 | Jokozeki |
| 2002/0077535 A1 | 6/2002 | Finarov et al. |
| 2002/0082486 A1 | 6/2002 | Lavery et al. |
| 2002/0082489 A1 | 6/2002 | Casciani et al. |

| | | | | | |
|---|---|---|---|---|---|
| 2002/0082665 A1 | 6/2002 | Haller et al. | 2003/0125616 A1 | 7/2003 | Black et al. |
| 2002/0084904 A1 | 7/2002 | De La Huerga | 2003/0132495 A1 | 7/2003 | Mills et al. |
| 2002/0087087 A1 | 7/2002 | Oka et al. | 2003/0135124 A1 | 7/2003 | Russell |
| 2002/0091335 A1 | 7/2002 | John et al. | 2003/0135127 A1 | 7/2003 | Sackner et al. |
| 2002/0091416 A1 | 7/2002 | Wassmund et al. | 2003/0137425 A1 | 7/2003 | Gabriel |
| 2002/0091417 A1 | 7/2002 | Splett et al. | 2003/0139641 A1 | 7/2003 | Hoedeman et al. |
| 2002/0095087 A1 | 7/2002 | Mourad et al. | 2003/0139656 A1 | 7/2003 | Kiani et al. |
| 2002/0095092 A1 | 7/2002 | Kondo et al. | 2003/0139680 A1 | 7/2003 | Sheldon |
| 2002/0099268 A1 | 7/2002 | Paul et al. | 2003/0143297 A1 | 7/2003 | Mills et al. |
| 2002/0099298 A1 | 7/2002 | Yokozeki | 2003/0144579 A1 | 7/2003 | Buss |
| 2002/0103445 A1 | 8/2002 | Rahdert et al. | 2003/0144584 A1 | 7/2003 | Mendelson |
| 2002/0109600 A1 | 8/2002 | Mault et al. | 2003/0149366 A1 | 8/2003 | Stringer et al. |
| 2002/0111543 A1 | 8/2002 | Penner et al. | 2003/0153834 A1 | 8/2003 | Miller |
| 2002/0111777 A1 | 8/2002 | David | 2003/0156288 A1 | 8/2003 | Barnum et al. |
| 2002/0115919 A1 | 8/2002 | Al-Ali | 2003/0159844 A1 | 8/2003 | Wolf et al. |
| 2002/0116797 A1 | 8/2002 | Modgil et al. | 2003/0162414 A1 | 8/2003 | Schulz et al. |
| 2002/0124295 A1 | 9/2002 | Fenwick et al. | 2003/0167080 A1 | 9/2003 | Hart et al. |
| 2002/0133066 A1 | 9/2002 | Miller et al. | 2003/0176810 A1 | 9/2003 | Maahs et al. |
| 2002/0133082 A1 | 9/2002 | Ogura | 2003/0181799 A1 | 9/2003 | Lindekugel et al. |
| 2002/0135488 A1 | 9/2002 | Hibbs et al. | 2003/0189492 A1 | 10/2003 | Harvie |
| 2002/0139368 A1 | 10/2002 | Bachinski | 2003/0208109 A1 | 11/2003 | David et al. |
| 2002/0148470 A1 | 10/2002 | Blue et al. | 2003/0208128 A1 | 11/2003 | Hamilton et al. |
| 2002/0151929 A1 | 10/2002 | Goto et al. | 2003/0210149 A1 | 11/2003 | Reisman et al. |
| 2002/0156353 A1 | 10/2002 | Larson | 2003/0212334 A1 | 11/2003 | Ogura et al. |
| 2002/0156354 A1 | 10/2002 | Larson | 2003/0214408 A1 | 11/2003 | Grajales et al. |
| 2002/0156503 A1 | 10/2002 | Powers et al. | 2003/0216659 A1 | 11/2003 | Brawner et al. |
| 2002/0161290 A1 | 10/2002 | Chance | 2003/0216728 A1 | 11/2003 | Stern et al. |
| 2002/0161305 A1 | 10/2002 | Oka | 2003/0217972 A1 | 11/2003 | Connell et al. |
| 2002/0161309 A1 | 10/2002 | Marro | 2003/0225323 A1 | 12/2003 | Kiani et al. |
| 2002/0165440 A1 | 11/2002 | Mason et al. | 2003/0229276 A1 | 12/2003 | Sarussi et al. |
| 2002/0165462 A1 | 11/2002 | Westbrook et al. | 2003/0230307 A1 | 12/2003 | DeVries et al. |
| 2002/0165590 A1 | 11/2002 | Crowe et al. | 2003/0233087 A1 | 12/2003 | Chen et al. |
| 2002/0173706 A1 | 11/2002 | Takatani | 2004/0002655 A1 | 1/2004 | Bolorforosh et al. |
| 2002/0173708 A1 | 11/2002 | Delonzer et al. | 2004/0004547 A1 | 1/2004 | Appelt et al. |
| 2002/0188206 A1 | 12/2002 | Davis et al. | 2004/0007585 A1 | 1/2004 | Griffith et al. |
| 2002/0193692 A1 | 12/2002 | Inukai et al. | 2004/0030258 A1 | 2/2004 | Williams et al. |
| 2003/0004445 A1 | 1/2003 | Hall et al. | 2004/0030323 A1 | 2/2004 | Ullestad et al. |
| 2003/0004547 A1 | 1/2003 | Owen et al. | 2004/0035208 A1 | 2/2004 | Diaz et al. |
| 2003/0009083 A1 | 1/2003 | Takahashi | 2004/0036854 A1 | 2/2004 | Fukuda et al. |
| 2003/0009092 A1 | 1/2003 | Parker | 2004/0039254 A1 | 2/2004 | Stivoric et al. |
| 2003/0009119 A1 | 1/2003 | Kamm et al. | 2004/0039272 A1 | 2/2004 | Abdul-Hafiz et al. |
| 2003/0009308 A1 | 1/2003 | Kirtley | 2004/0044286 A1 | 3/2004 | Hossack et al. |
| 2003/0018243 A1 | 1/2003 | Gerhardt et al. | 2004/0044545 A1 | 3/2004 | Wiesmann et al. |
| 2003/0023140 A1 | 1/2003 | Chance | 2004/0047210 A1 | 3/2004 | Iwasaki |
| 2003/0023146 A1 | 1/2003 | Shusterman | 2004/0054287 A1 | 3/2004 | Stephens |
| 2003/0023277 A1 | 1/2003 | Owen et al. | 2004/0054289 A1 | 3/2004 | Eberle et al. |
| 2003/0028105 A1 | 2/2003 | Miller | 2004/0054291 A1 | 3/2004 | Schulz et al. |
| 2003/0032887 A1 | 2/2003 | Harada et al. | 2004/0064097 A1 | 4/2004 | Peterson |
| 2003/0032988 A1 | 2/2003 | Fincke | 2004/0064165 A1 | 4/2004 | Thompson |
| 2003/0040779 A1 | 2/2003 | Engmark et al. | 2004/0082842 A1 | 4/2004 | Lumba et al. |
| 2003/0040820 A1 | 2/2003 | Stover et al. | 2004/0088027 A1 | 5/2004 | Burnes et al. |
| 2003/0045785 A1 | 3/2003 | Diab et al. | 2004/0092919 A1 | 5/2004 | Ritchie et al. |
| 2003/0045806 A1 | 3/2003 | Brydon | 2004/0100784 A1 | 5/2004 | Willers et al. |
| 2003/0050551 A1 | 3/2003 | Shabty et al. | 2004/0102931 A1 | 5/2004 | Ellis et al. |
| 2003/0055308 A1 | 3/2003 | Friemel et al. | 2004/0114659 A1 | 6/2004 | Quinn et al. |
| 2003/0062046 A1 | 4/2003 | Wiesmann et al. | 2004/0117891 A1 | 6/2004 | Hannula et al. |
| 2003/0065269 A1 | 4/2003 | Vetter et al. | 2004/0122302 A1 | 6/2004 | Mason et al. |
| 2003/0065273 A1 | 4/2003 | Mault et al. | 2004/0133088 A1 | 7/2004 | Al-Ali |
| 2003/0065274 A1 | 4/2003 | Mault et al. | 2004/0144391 A1 | 7/2004 | Brady et al. |
| 2003/0065275 A1 | 4/2003 | Mault et al. | 2004/0147822 A1 | 7/2004 | Al-Ali et al. |
| 2003/0066672 A1 | 4/2003 | Watchko et al. | 2004/0147823 A1 | 7/2004 | Kiani et al. |
| 2003/0069508 A1 | 4/2003 | Kawaguchi et al. | 2004/0147974 A1 | 7/2004 | Engmark et al. |
| 2003/0074037 A1 | 4/2003 | Moore et al. | 2004/0149282 A1 | 8/2004 | Hickle |
| 2003/0086156 A1 | 5/2003 | McGuire, Jr. | 2004/0158303 A1 | 8/2004 | Lennox et al. |
| 2003/0088203 A1 | 5/2003 | Gelfand et al. | 2004/0160144 A1 | 8/2004 | Daft et al. |
| 2003/0088385 A1 | 5/2003 | David | 2004/0162494 A1 | 8/2004 | Ogura et al. |
| 2003/0092999 A1 | 5/2003 | Goto et al. | 2004/0163648 A1 | 8/2004 | Burton |
| 2003/0097074 A1 | 5/2003 | Oka et al. | 2004/0168519 A1 | 9/2004 | Kalvensten et al. |
| 2003/0105403 A1 | 6/2003 | Istvan et al. | 2004/0173456 A1 | 9/2004 | Boos et al. |
| 2003/0116159 A1 | 6/2003 | Orr et al. | 2004/0186390 A1 | 9/2004 | Ross et al. |
| 2003/0120183 A1 | 6/2003 | Simmons | 2004/0221370 A1 | 11/2004 | Hannula et al. |
| 2003/0120271 A1 | 6/2003 | Burnside et al. | 2004/0230108 A1 | 11/2004 | Melker et al. |
| 2003/0122706 A1 | 7/2003 | Choi et al. | 2004/0230116 A1 | 11/2004 | Cowan et al. |

| | | | | | |
|---|---|---|---|---|---|
| 2004/0231772 A1 | 11/2004 | Leonard et al. | 2006/0009698 A1 | 1/2006 | Banet et al. |
| 2004/0236207 A1 | 11/2004 | Widener et al. | 2006/0011199 A1 | 1/2006 | Rashad et al. |
| 2004/0236224 A1 | 11/2004 | Stringer et al. | 2006/0020181 A1 | 1/2006 | Schmitt |
| 2004/0236242 A1 | 11/2004 | Graham et al. | 2006/0030049 A1 | 2/2006 | Bhimani et al. |
| 2004/0242981 A1 | 12/2004 | Pattisapu | 2006/0030767 A1 | 2/2006 | Lang et al. |
| 2004/0252750 A1 | 12/2004 | Gruszecki et al. | 2006/0036179 A1 | 2/2006 | Miller |
| 2004/0254490 A1 | 12/2004 | Egli | 2006/0047447 A1 | 3/2006 | Brady et al. |
| 2004/0254501 A1 | 12/2004 | Mault | 2006/0058593 A1 | 3/2006 | Drinan et al. |
| 2004/0254569 A1 | 12/2004 | Brosch et al. | 2006/0058690 A1 | 3/2006 | Bartnik et al. |
| 2004/0260161 A1 | 12/2004 | Melker et al. | 2006/0064133 A1 | 3/2006 | Von Arx et al. |
| 2004/0260191 A1 | 12/2004 | Stubbs et al. | 2006/0064134 A1 | 3/2006 | Mazar et al. |
| 2004/0263337 A1 | 12/2004 | Terauchi et al. | 2006/0064142 A1 | 3/2006 | Chavan et al. |
| 2004/0267104 A1 | 12/2004 | Hannula et al. | 2006/0064143 A1 | 3/2006 | Von Arx et al. |
| 2004/0267145 A1 | 12/2004 | David et al. | 2006/0072645 A1 | 4/2006 | Quinn et al. |
| 2005/0001728 A1 | 1/2005 | Appelt et al. | 2006/0074283 A1 | 4/2006 | Henderson et al. |
| 2005/0012617 A1 | 1/2005 | DiSilvestro et al. | 2006/0074324 A1 | 4/2006 | Wu et al. |
| 2005/0015653 A1 | 1/2005 | Hajji et al. | 2006/0084848 A1 | 4/2006 | Mitchnick |
| 2005/0017864 A1 | 1/2005 | Tsoukalis | 2006/0084852 A1 | 4/2006 | Mason et al. |
| 2005/0020919 A1 | 1/2005 | Stringer et al. | 2006/0085227 A1 | 4/2006 | Rosenfeld et al. |
| 2005/0027207 A1 | 2/2005 | Westbrook et al. | 2006/0095032 A1 | 5/2006 | Jackson et al. |
| 2005/0029432 A1 | 2/2005 | Bacarella et al. | 2006/0100496 A1 | 5/2006 | Avron |
| 2005/0041531 A1 | 2/2005 | Sekura | 2006/0100530 A1 | 5/2006 | Kliot et al. |
| 2005/0043599 A1 | 2/2005 | O'Mara | 2006/0100618 A1 | 5/2006 | Chan et al. |
| 2005/0043763 A1 | 2/2005 | Marcovecchio et al. | 2006/0122517 A1 | 6/2006 | Banet et al. |
| 2005/0046575 A1 | 3/2005 | Cooper et al. | 2006/0122520 A1 | 6/2006 | Banet et al. |
| 2005/0049465 A1 | 3/2005 | Wang | 2006/0124128 A1 | 6/2006 | Deane et al. |
| 2005/0049501 A1 | 3/2005 | Conero et al. | 2006/0125623 A1 | 6/2006 | Appelt et al. |
| 2005/0059869 A1 | 3/2005 | Scharf et al. | 2006/0132382 A1 | 6/2006 | Jannard |
| 2005/0070776 A1 | 3/2005 | Mannheimer et al. | 2006/0133362 A1 | 6/2006 | Stein et al. |
| 2005/0070778 A1 | 3/2005 | Lackey et al. | 2006/0142640 A1 | 6/2006 | Takahashi |
| 2005/0070813 A1 | 3/2005 | Donofrio et al. | 2006/0149132 A1 | 7/2006 | Iddan |
| 2005/0075550 A1 | 4/2005 | Lindekugel | 2006/0149339 A1 | 7/2006 | Burnes et al. |
| 2005/0080345 A1 | 4/2005 | Finburgh et al. | 2006/0167351 A1 | 7/2006 | Isaacson et al. |
| 2005/0085799 A1 | 4/2005 | Luria et al. | 2006/0173247 A1 | 8/2006 | Medina |
| 2005/0090754 A1 | 4/2005 | Wolff et al. | 2006/0183980 A1 | 8/2006 | Yang |
| 2005/0096557 A1 | 5/2005 | Vosburgh et al. | 2006/0184051 A1 | 8/2006 | Hempstead et al. |
| 2005/0102167 A1 | 5/2005 | Kapoor | 2006/0189859 A1 | 8/2006 | Kiani et al. |
| 2005/0113650 A1 | 5/2005 | Paciohe et al. | 2006/0195026 A1 | 8/2006 | Casciani et al. |
| 2005/0113656 A1 | 5/2005 | Chance | 2006/0195027 A1 | 8/2006 | Casciani et al. |
| 2005/0113703 A1 | 5/2005 | Farringdon et al. | 2006/0195028 A1 | 8/2006 | Hannula et al. |
| 2005/0114154 A1 | 5/2005 | Wolkowicz et al. | 2006/0211929 A1 | 9/2006 | Casciani et al. |
| 2005/0154299 A1 | 7/2005 | Hoctor et al. | 2006/0211942 A1 | 9/2006 | Hoctor et al. |
| 2005/0171576 A1 | 8/2005 | Williams et al. | 2006/0217604 A1 | 9/2006 | Fein et al. |
| 2005/0182458 A1 | 8/2005 | Goedeke | 2006/0217605 A1 | 9/2006 | Fein et al. |
| 2005/0188991 A1 | 9/2005 | Sun et al. | 2006/0217606 A1 | 9/2006 | Fein et al. |
| 2005/0190068 A1 | 9/2005 | Gentry et al. | 2006/0217607 A1 | 9/2006 | Fein et al. |
| 2005/0197548 A1 | 9/2005 | Dietiker | 2006/0217608 A1 | 9/2006 | Fein et al. |
| 2005/0197550 A1 | 9/2005 | Al-Ali et al. | 2006/0224040 A1 | 10/2006 | Khait et al. |
| 2005/0206518 A1 | 9/2005 | Welch et al. | 2006/0224326 A1 | 10/2006 | St. Ores et al. |
| 2005/0215847 A1 | 9/2005 | Heruth et al. | 2006/0224421 A1 | 10/2006 | St. Ores et al. |
| 2005/0215880 A1 | 9/2005 | Harrison et al. | 2006/0229510 A1 | 10/2006 | Fein et al. |
| 2005/0215947 A1 | 9/2005 | Heruth et al. | 2006/0229511 A1 | 10/2006 | Fein et al. |
| 2005/0216064 A1 | 9/2005 | Heruth et al. | 2006/0229517 A1 | 10/2006 | Lin et al. |
| 2005/0216199 A1 | 9/2005 | Banet | 2006/0241358 A1 | 10/2006 | Al-Ali et al. |
| 2005/0222522 A1 | 10/2005 | Heruth et al. | 2006/0241384 A1 | 10/2006 | Fisher et al. |
| 2005/0222643 A1 | 10/2005 | Heruth et al. | 2006/0241510 A1 | 10/2006 | Halperin et al. |
| 2005/0228234 A1 | 10/2005 | Yang | 2006/0247504 A1 | 11/2006 | Tice |
| 2005/0228296 A1 | 10/2005 | Banet | 2006/0253010 A1 | 11/2006 | Brady et al. |
| 2005/0228297 A1 | 10/2005 | Banet et al. | 2006/0253953 A1 | 11/2006 | Williams |
| 2005/0231686 A1 | 10/2005 | Rathjen | 2006/0258922 A1 | 11/2006 | Mason et al. |
| 2005/0234312 A1 | 10/2005 | Suzuki et al. | 2006/0264722 A1 | 11/2006 | Hannula et al. |
| 2005/0234317 A1 | 10/2005 | Kiani | 2006/0264723 A1 | 11/2006 | Hannula et al. |
| 2005/0234518 A1 | 10/2005 | Heruth et al. | 2006/0264724 A1 | 11/2006 | Hannula et al. |
| 2005/0240087 A1 | 10/2005 | Keenan et al. | 2006/0264725 A1 | 11/2006 | Hannula et al. |
| 2005/0245797 A1 | 11/2005 | Al-Ali et al. | 2006/0264726 A1 | 11/2006 | Mannheimer et al. |
| 2005/0256523 A1 | 11/2005 | Chen et al. | 2006/0264727 A1 | 11/2006 | Mannheimer et al. |
| 2005/0261594 A1 | 11/2005 | Banet | 2006/0264771 A1 | 11/2006 | Lin et al. |
| 2005/0268916 A1 | 12/2005 | Mumford et al. | 2006/0276700 A1 | 12/2006 | O'Neil et al. |
| 2005/0272986 A1 | 12/2005 | Smith et al. | 2006/0276701 A1 | 12/2006 | Ray |
| 2005/0277819 A1 | 12/2005 | Kiani et al. | 2006/0281984 A1 | 12/2006 | Mannheimer et al. |
| 2005/0277821 A1 | 12/2005 | Payne, Jr. | 2007/0032732 A1 | 2/2007 | Shelley et al. |
| 2005/0283082 A1 | 12/2005 | Geddes et al. | 2007/0149871 A1 | 6/2007 | Sarussi et al. |
| 2006/0009685 A1 | 1/2006 | Finarov et al. | 2007/0293746 A1 | 12/2007 | Sarussi et al. |

| | | | | | | |
|---|---|---|---|---|---|---|
| 2008/0009691 | A1 | 1/2008 | Parker | JP | 2004/065832 A | 3/2004 |
| 2008/0076988 | A1 | 3/2008 | Sarussi et al. | JP | 2004/121549 A | 4/2004 |
| 2008/0076990 | A1 | 3/2008 | Sarussi et al. | JP | 2004258761 A | 9/2004 |

FOREIGN PATENT DOCUMENTS

| | | |
|---|---|---|
| JP | 2005/013612 A | 1/2005 |
| JP | 2005/110816 A | 4/2005 |
| CN | 1657007 | 8/2005 |
| JP | 2005/111187 A | 4/2005 |
| DE | 3705493 | 8/1988 |
| JP | 2005/143782 A | 5/2005 |
| DE | 3744781 A1 | 1/1989 |
| JP | 2005/168600 A | 6/2005 |
| DE | 3810411 A1 | 10/1989 |
| JP | 2005/266860 A | 9/2005 |
| DE | 3927038 | 2/1991 |
| JP | 2006/061178 A | 3/2006 |
| DE | 4429845 C1 | 10/1995 |
| JP | 2006/066512 A | 3/2006 |
| DE | 19541605 A1 | 5/1997 |
| JP | 2006/122693 A | 5/2006 |
| DE | 19939302 | 5/2001 |
| KR | 2003-195176 | 8/2002 |
| DE | 10029205 | 1/2002 |
| KR | 2005-292552 | 12/2004 |
| EP | 0268850 | 6/1988 |
| RU | 2000-337592 C1 | 6/1999 |
| EP | 0 313 238 A1 | 10/1988 |
| RU | 2132204 | 6/1999 |
| EP | 0338518 | 10/1989 |
| WO | WO9001293 | 2/1990 |
| EP | 0463620 | 1/1992 |
| WO | WO9111137 | 8/1991 |
| EP | 0 573 137 A1 | 2/1993 |
| WO | WO 91/15151 A1 | 10/1991 |
| EP | 0543172 A2 | 5/1993 |
| WO | WO 91/18550 | 12/1991 |
| EP | 0 572 684 A1 | 8/1993 |
| WO | WO 92/20273 | 11/1992 |
| EP | 0578530 | 1/1994 |
| WO | WO 95/06430 | 3/1995 |
| EP | 0580385 A1 | 1/1994 |
| WO | WO9512349 | 5/1995 |
| EP | 0621026 A2 | 10/1994 |
| WO | WO 96/15714 | 5/1996 |
| EP | 0631756 | 1/1995 |
| WO | WO 96/16591 A1 | 6/1996 |
| EP | 0665025 A2 | 8/1995 |
| WO | WO 96/41138 A1 | 12/1996 |
| EP | 0 721 110 A1 | 7/1996 |
| WO | WO 97/20494 | 6/1997 |
| EP | 1 683 478 A1 | 10/1999 |
| WO | WO 97/20497 A1 | 6/1997 |
| EP | 0 695 139 A1 | 12/1999 |
| WO | WO9817174 | 4/1998 |
| EP | 0996063 | 4/2000 |
| WO | WO9947039 | 9/1999 |
| EP | 1048323 A2 | 11/2000 |
| WO | WO 99/63883 | 12/1999 |
| EP | 1 169 965 A1 | 6/2001 |
| WO | WO0059374 | 10/2000 |
| EP | 1130412 A2 | 9/2001 |
| WO | WO 00/78209 A1 | 12/2000 |
| EP | 0775311 B1 | 7/2002 |
| WO | WO 01/01855 A1 | 1/2001 |
| FR | 2555744 | 5/1985 |
| WO | WO 01/17425 A2 | 3/2001 |
| FR | 002601137 A1 | 1/1988 |
| WO | WO0176471 | 10/2001 |
| GB | 834469 | 5/1960 |
| WO | WO 01/87224 A1 | 11/2001 |
| GB | 2135074 A | 8/1984 |
| WO | WO 02/15784 A1 | 2/2002 |
| GB | 2390903 A | 1/2004 |
| WO | WO 02/065901 A2 | 8/2002 |
| JP | 55024614 A | 2/1980 |
| WO | WO 02/066977 A1 | 8/2002 |
| JP | 07336597 A | 12/1985 |
| WO | WO 02/089664 | 11/2002 |
| JP | 04057161 A | 2/1992 |
| WO | WO 02/089664 A2 | 11/2002 |
| JP | 08111295 A | 4/1996 |
| WO | WO 03/026558 A2 | 4/2003 |
| JP | 08112257 A | 5/1996 |
| WO | WO 03/057030 A1 | 7/2003 |
| JP | 08336546 A | 12/1996 |
| WO | WO03071928 | 9/2003 |
| JP | 09010319 A | 1/1997 |
| WO | WO 03/080152 A1 | 10/2003 |
| JP | 9154937 A | 6/1997 |
| WO | WO 2004/030480 A1 | 4/2004 |
| JP | 10314149 A | 12/1998 |
| WO | WO 2004/046673 A1 | 6/2004 |
| JP | 11259583 A | 9/1999 |
| WO | WO 2004/084720 A2 | 10/2004 |
| JP | 2000/189440 A | 7/2000 |
| WO | WO 2005/046466 A1 | 5/2005 |
| JP | 2001/161648 A | 6/2001 |
| WO | WO 2005/079663 A1 | 9/2005 |
| JP | 2001-190498 A | 7/2001 |
| WO | WO 2006/007231 | 1/2006 |
| JP | 2001-308576 A | 11/2001 |
| WO | WO 2006/017117 A1 | 2/2006 |
| JP | 2001-332832 A | 11/2001 |
| WO | WO 2006/021956 A2 | 3/2006 |
| JP | 2001/346775 A | 12/2001 |
| WO | WO 2006/094108 A1 | 8/2006 |
| JP | 2002/065647 A | 3/2002 | | | |
| JP | 2003/210402 A | 7/2003 | | | |
| JP | 2003/235813 A | 8/2003 | | | |
| JP | 2003/265425 A | 9/2003 | | | |
| JP | 2004-16659 A | 1/2004 | | | |

OTHER PUBLICATIONS

U.S. Appl. No. 10/779,331, filed Feb. 13, 2004, Hannula et al.
U.S. Appl. No. 11/358,868, filed Feb. 21, 2006, Hannula et al.

* cited by examiner

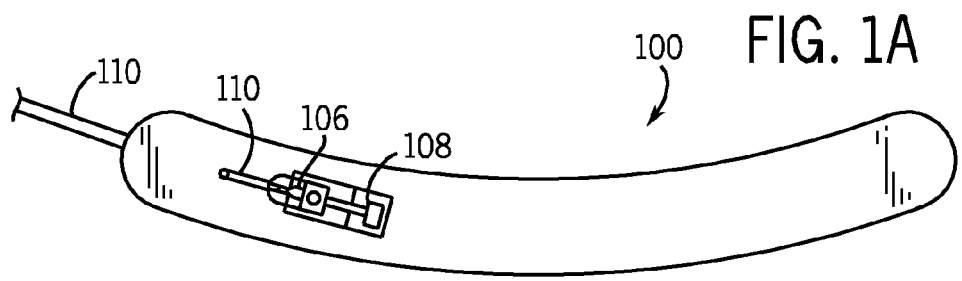
FIG. 1A
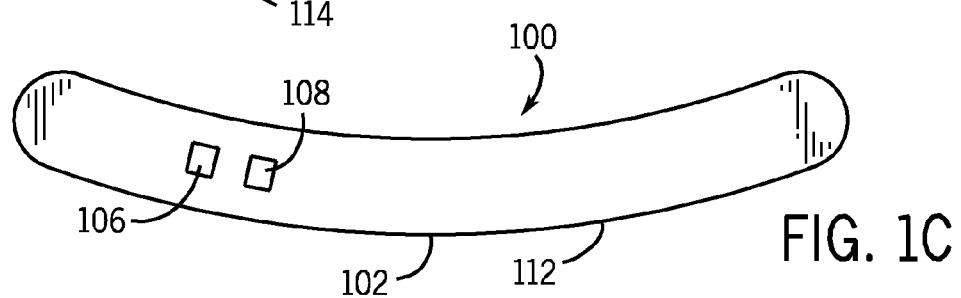
FIG. 1B
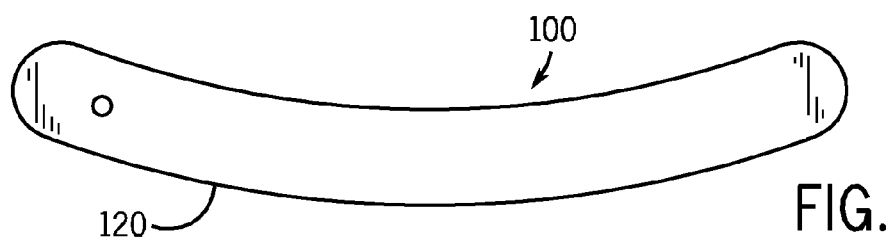
FIG. 1C
FIG. 1D
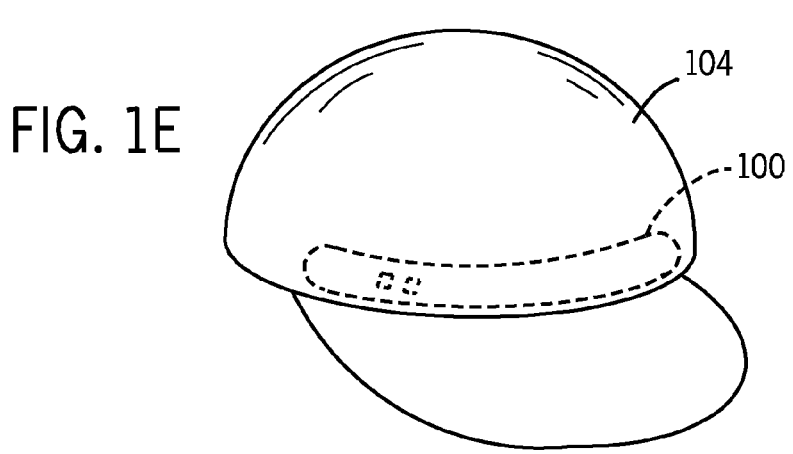
FIG. 1E

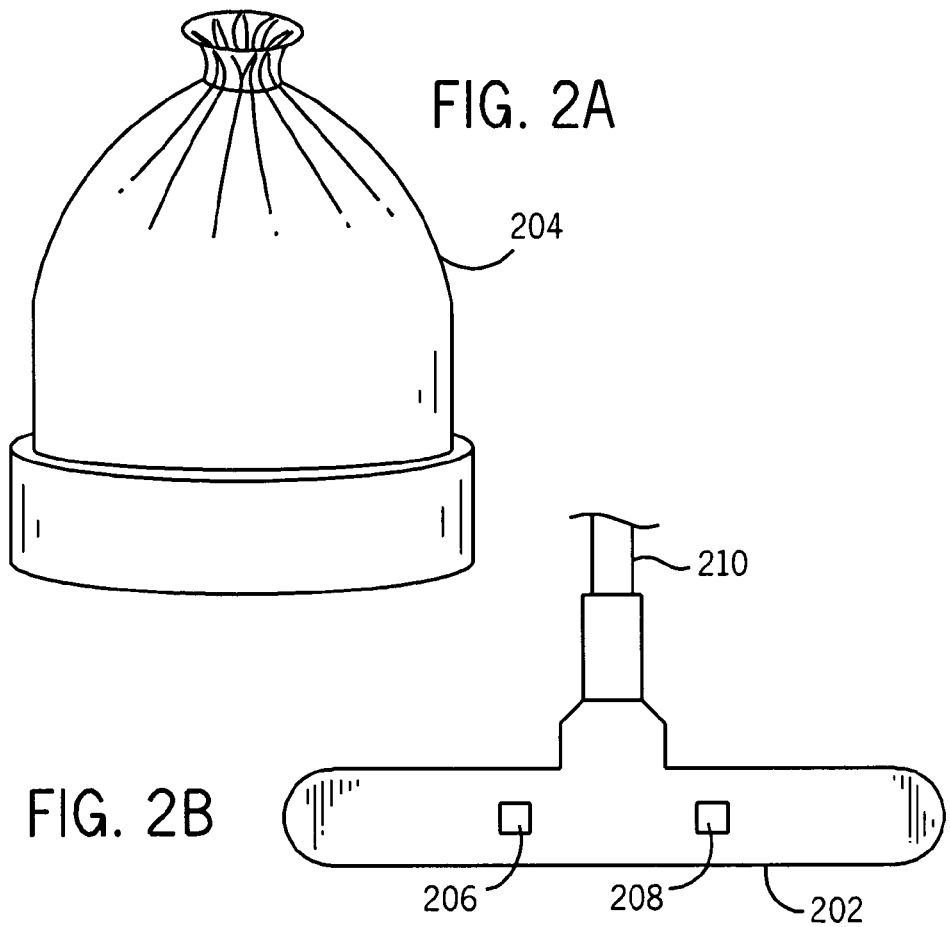
FIG. 2A
FIG. 2B
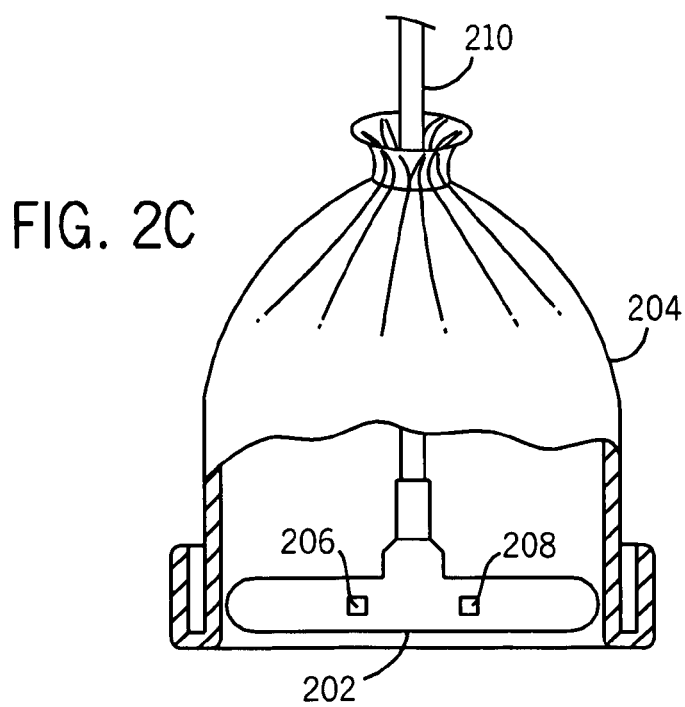
FIG. 2C

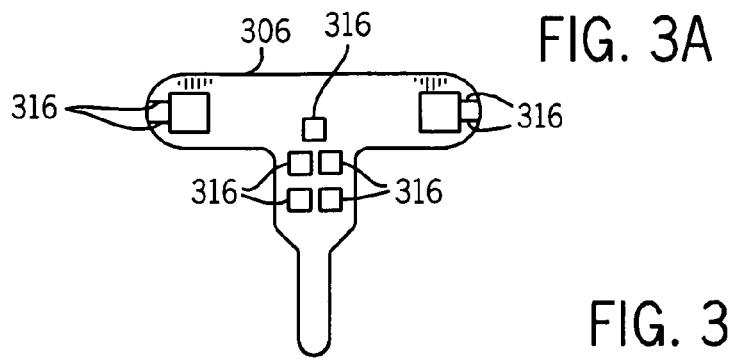
FIG. 3A
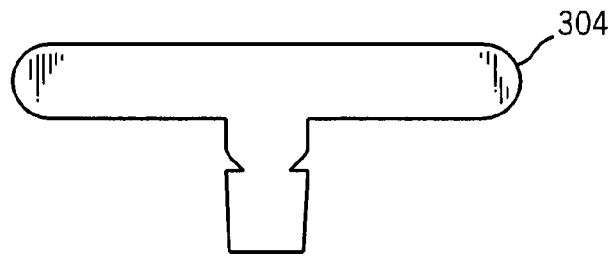
FIG. 3B
FIG. 3C
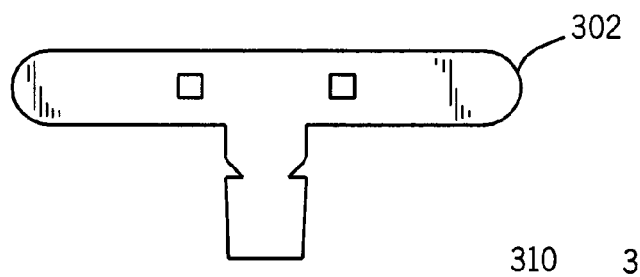
FIG. 3D
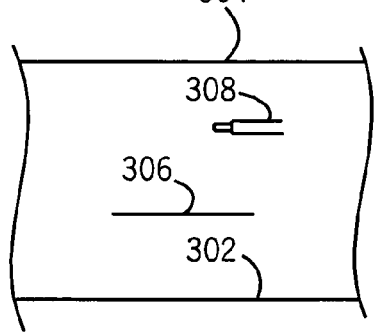
FIG. 3F
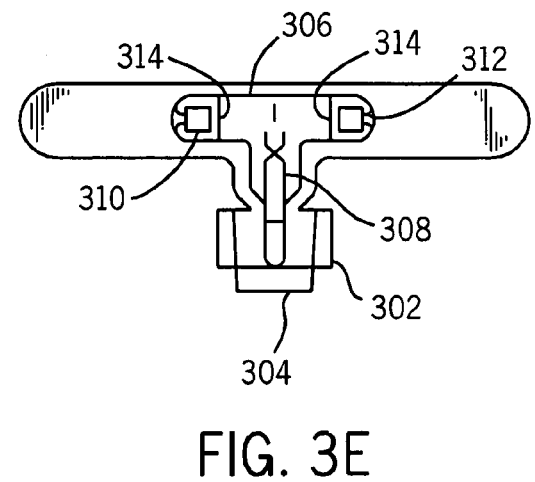
FIG. 3E

HAT-BASED OXIMETER SENSOR

CROSS REFERENCE TO RELATED APPLICATIONS

This application is a continuation of U.S. application Ser. No. 11/358,868 filed Feb. 21, 2006, the specification of which is hereby incorporated by reference in its entirety, which is a divisional of prior U.S. application Ser. No. 10/606,668, filed Jun. 25, 2003, now U.S. Pat. No. 7,047,056 issued May 16, 2006, the specification of which is incorporated by reference in its entirety.

BACKGROUND OF THE INVENTION

Field of the Invention

The present invention relates to optical oximeter sensors, and in particular to hat-based pulse oximeter sensors.

Many types of optical sensors are used to measure physiological characteristics of a patient. Typically, an optical sensor provides emitted light which is then scattered through a portion of a patient's tissue and detected. Various characteristics of a patient can be determined from analyzing such light, such as oxygen saturation, pulse rate, tissue bilirubin, etc.

Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which scatters light through a portion of the patient's tissue where blood perfuses the tissue, and photoelectrically senses the absorption of light in such tissue. The amount of light absorbed is then used to calculate the amount of blood constituent being measured.

The light scattered through the tissue is selected to be of one or more wavelengths that are absorbed by the blood in an amount representative of the amount of the blood constituent present in the blood. The amount of transmitted light scattered through the tissue will vary in accordance with the changing amount of blood constituent in the tissue and the related light absorption. For measuring blood oxygen level, such sensors have typically been provided with a light source that is adapted to generate light of at least two different wavelengths, and with photodetectors sensitive to both of those wavelengths, in accordance with known techniques for measuring blood oxygen saturation.

Known non-invasive sensors include devices that are secured to a portion of the body, such as a finger, an ear or the scalp. In animals and humans, the tissue of these body portions is perfused with blood and the tissue surface is readily accessible to the sensor.

Certain types of oximeter sensors are applied to a patient's forehead. To aid in the sensor's proper placement and the proper application of pressure by the sensor to the forehead site, some forehead sensors are maintained at the forehead site by either the assistance of an adhesive layer and/or a headband. While these approaches are helpful, there is still a need for an improved and easy way of placing, retaining, and locating the sensor on the forehead of its user.

BRIEF SUMMARY OF THE INVENTION

The present invention provides an oximeter sensor which will attach to a patient's forehead in an improved manner. In certain embodiments, the securing of the sensor to the forehead of the patient is achieved by attaching the sensor to the inside of hat which is worn by the patient when the sensor is in use.

In one embodiment, the present invention is an oximeter sensor, having: a substrate having a shape similar to a shape of at least a portion of a patient's forehead and including a section adapted to substantially fit over a portion of a forehead of a patient; an emitter disposed on the substrate at a position located on the section; and a detector disposed on the substrate at a distance from the emitter.

In one embodiment, the substrate is resilient and has a shape conformable to the forehead of a patient.

In one embodiment, the substrate includes an adhesive layer for adhering to the forehead of a patient.

In one embodiment, a hat is used for holding the sensor against the patient's forehead.

In one embodiment, the substrate is adhered to the inside of said hat.

In one embodiment, the substrate is adhesively attached to the inside of the hat. Alternately, the substrate is sewn into the hat.

In another embodiment, the present invention provides a method for determination of a blood characteristic, including: applying an emitter and a detector to spaced-apart positions on a forehead of a patient in the lower forehead region, above the eyebrow, with both the detector and the emitter placed above and predominantly lateral of the iris; securing the emitter and detector to the patient; emitting electromagnetic radiation with the emitter; detecting electromagnetic radiation scattered by the tissues of the forehead by the detector and producing a detector signal; and determining a blood characteristic in the patient from the detector signal.

In one embodiment, the securing of the emitter and the detector to the patient's forehead is achieved by attaching the emitter and the detector to an inside of a hat, and placing the hat on the head of the patient.

For a further understanding of the nature and advantages of the present invention, reference should be made to the following description in conjunction with the accompanying drawings.

BRIEF DESCRIPTION OF THE DRAWINGS

FIGS. 1A-1E are assembly drawings of an embodiment of the sensor in accordance with the present invention that can be placed within a hat or cap.

FIGS. 2A-2C are drawings of a stocking hat, with an embodiment of the sensor in accordance with the present invention shown mounted in the hat.

FIGS. 3A-3F are assembly drawings of an embodiment of the sensor of FIGS. 1 or 2.

DETAILED DESCRIPTION OF THE INVENTION

The embodiments of the present invention are directed towards configuring a reflectance-type oximeter sensor for placement in a hat in order to provide a relatively easy means of placing, retaining, and locating the sensor on the forehead of the user. With regard to the location of the sensor on the patient's forehead, it is preferred to have the sensor be located on the lower forehead region, above the eyebrow, with the sensor optics (emitter and detector) located above and predominantly lateral to or centered over the iris. The oximeter sensor can be attached to the inside band of a hat. The precise location of the reflectance sensor in the hat allows appropriate placement of the sensor in the optimal forehead location by a user not skilled in sensor placement. It has been found that the placement of a reflectance forehead sensor is a factor in the accurate determination of a blood flow characteristic, due to the vasculature of the forehead. In addition, it has been shown that having a certain amount of pressure on the forehead sensor can reduce the incidence of venous pulsations effects on the oximeter reading. The placement of the sensor in the band of the hat would minimize these issues, as the placement of a hat is fairly repeatable and predictable. A hat-based oximeter sensor as embodied by the present invention can be used on patients in clinical settings, or by athletes, soldiers, firemen, or in any environment where information related to a physiological parameter, such as heart rate or oxygen saturation information is desired.

FIGS. 1A-1E are assembly drawings of an embodiment of the sensor in accordance with the present invention that can be placed within a hat or cap. This figure shows an oximeter sensor placed on a substrate 102 that can be placed or adhered to the inside of a hat 104. In the hat-based embodiment, the sensor uses an emitter 106 containing two discrete wavelengths and a detector 108 placed more than 2 mm away, and ideally 10 mm-15 mm from the emitter. The surface 102 can be black in order to minimize any shunting of light between sensor and patient skin. The sensor in a hat could be used in conjunction with a small, portable oximeter to allow mobility of the user during activities. Similarly, the sensor could be incorporated into a headband. Alternately, it may be desirable to provide a sensor with adhesive backing that would allow the user to place the sensor in a hat of their choice. Also shown in FIG. 1 is a cable 110 for providing drive current to the LED and for providing the detector signal to the oximeter. The cable provides the electrical connection to the monitor; it also provides power for the emitter, signal carrying conductors from the detector, and shielding to protect the small signals from the detector against external electrical interference.

The sensor is shown in a multi-layer structure having a face portion 112. The face 112 is the surface that is placed against the patient's skin. The face material may have an adhesive layer such as an acrylic or synthetic rubber adhesive, or it may be without adhesive, and typically made from a foam PVC or foam polyurethane material. The face 112 component is preferably black so as to minimize the incidence of reflected light that does not go through the tissue. Below the face layer 112 are two windows 114. The windows 114 are generally a clear component, such as for example, a thin film or a clear molded plastic component that makes contact with the skin. The thin film window may be a polyurethane or an acrylic adhesive on a polyester film. The intent of the window 114 is to provide an efficient optical coupling mechanism between the optical components (emitter and detector) and the skin. Located above the face 114, is a Faraday shield 116. The Faraday shield 116 is a conductive material, for example, a copper film or copper mesh, which is electrically connected to the monitor ground to help shield the detector from extraneous electrical interference while passing light to the detector. Next located are the LED 106 and the detector 108. Above the LED and the detector is a mask layer, which may include more than one mask layer. The mask layer 118 is generally a thin film that is intended to block light from entering the back side of the sensor, or from traveling directly from emitter to detector (shunt light). The purpose of the mask 118 is to ensure that all of the light reaching the detector is light from the emitter that has traveled through the capillary bed. Above the mask layer 118 is the back layer 120. The back or the top layer is the non-tissue contacting surface of the sensor. This layer may include a cosmetic finish for the sensor, which can be white with some printed artwork identifying the sensor. Typical materials may be Velcro loop, or soft PVC foam. In a case where the sensor is mounted inside a hat or cap, the top layer is sometimes referred to as the back layer. In this case, the back layer may include a double stick adhesive so that it can be mounted inside the hat.

FIGS. 2A-2C show a stocking hat, with an embodiment of the sensor in accordance with the present invention shown mounted in the hat. This alternate embodiment of the present invention is directed towards the placement of a small reflectance sensor 202 in a stocking cap or beanie 204. FIGS. 2A-2C show the sensor carrier layer 202 holding an LED 206 and a detector 208 and a cable 210, similar to the ones described above in conjunction with FIG. 1. This embodiment may be used for neonates. This embodiment would allow easy placement of a sensor on the forehead of a patient while applying a predictable pressure on the sensor. The sensor in a hat also resolves a concern about the cosmetic appearance of having a sensor on the forehead of the patient. A sensor in a stocking cap is much more acceptable to a parent than having a sensor located on the forehead. Depending on the tension of the stocking cap, provided by its own stretchiness or by an adjustable integral headband strap, the sensor may have a light tack adhesive, or no adhesive at all. The lack of an adhesive layer is a desirable feature, especially on neonates as adhesives may sometimes leave visible damage to the fragile skin of a neonate.

FIGS. 3A-3F are assembly drawings for an embodiment of the sensor of FIGS. 1 or 2. FIGS. 3A-3F show that the sensor portion generally includes a face layer 302, a top layer 304 and a flex circuit 306 that is placed between the face and top layers. Also shown in FIG. 3 is a multi-layer unassembled view showing the relative positions of the face 302, flex circuit 306, a cable 308 and the top layer 304. The flex circuit layer 306 holds the emitter (LED) 310 and the detector 312 as well as the mask layer 314 and Faraday shield as described above. The flex circuit 306 also has several holes 316 to allow for electrical connections between the leads in the cable and the LED and the detector.

As will be understood by those skilled in the art, the present invention may be embodied in other specific forms without departing from the essential characteristics thereof. For example, the sensor may include adhesive layers for adhering to the inside of a hat or the user's skin, or that that the sensor may be sewn into the hat. These other embodiments are intended to be included within the scope of the present invention, which is set forth in the following claims.

What is claimed is:

1. A sensor comprising:
   a stocking cap;
   a substrate disposed on the stocking cap;
   at least one sensing component disposed on the substrate; and
   an electrical connector coupled to the at least one sensing component, wherein the electrical connector extends from the substrate through an open portion of the stocking cap, wherein the open portion of the stocking cap is adapted to guide the electrical connector away from a patient's torso and is configured to be proximate to a top of the stocking cap when the stocking cap is applied to the patient.

2. The sensor of claim 1, wherein the substrate is conformable to a forehead-contacting surface of the stocking cap.

3. The sensor of claim 1, wherein the substrate comprises an adhesive layer adapted to attach the substrate to the stocking cap.

4. The sensor of claim 1, wherein the stocking cap comprises a neonatal stocking cap.

5. The sensor of claim 1, wherein the at least one sensing component is adapted to be attached to a forehead-contacting surface of the stocking cap.

6. The sensor of claim 1, wherein the electrical connector is secured by a portion of the stocking cap.

7. The sensor of claim 1, wherein the at least a portion of the electrical connector comprises a cable.

8. The sensor of claim 1, wherein the at least one sensing component comprises at least one of an emitter or a detector.

9. A method of manufacturing a cap-based sensor comprising:
   providing a stocking cap;
   providing a substrate disposed on the stocking cap;
   providing at least one sensing component disposed on the substrate; and
   providing an electrical connector coupled to the at least one sensing component, wherein the electrical connector extends from the substrate through an open portion of the stocking cap, wherein the open portion of the stocking cap is adapted to guide the electrical connector away from a patient's torso and is configured to be proximate to a top of the stocking cap when the stocking cap is applied to the patient.

10. The method of claim 9, wherein the substrate is conformable to a forehead-contacting surface of the stocking cap.

11. The method of claim 9, comprising providing an adhesive layer adapted to attach the substrate to the stocking cap.

12. The method of claim 9, wherein the stocking cap comprises a neonatal stocking cap.

13. The method of claim 9, wherein the at least one sensing component is adapted to be attached to a forehead-contacting surface of the stocking cap.

14. The method of claim 9, comprising providing an opening adapted to accommodate the at least one sensing component.

15. The method of claim 14, wherein the opening comprises a hole or a pocket.

16. The method of claim 9, wherein the electrical connector is secured by a portion of the stocking cap.

17. The method of claim 9, wherein the at least a portion of the electrical connector comprises a cable.

18. The method of claim 9, wherein the sensing component comprises at least one of an emitter or a detector.

19. A method of applying a sensor comprising:
   applying a stocking cap to a patient, wherein the stocking cap comprises a substrate and at least one sensing component disposed on the substrate, wherein an electrical connector coupled to the at least one sensing component extends through an open portion of the stocking cap away from the patient's torso, and wherein the open portion of the stocking cap is configured to be proximate to a top of the stocking cap when the stocking cap is applied to the patient.

* * * * *